United States Patent [19]

Findeisen et al.

[11] Patent Number: 5,194,084
[45] Date of Patent: Mar. 16, 1993

[54] HERBICIDAL SUBSTITUTED TRIAZOLONES

[75] Inventors: Kurt Findeisen, Odenthal; Markus Lindig, Hilden; Hans-Joachim Santel, Leverkusen; Robert R. Schmidt; Klaus Lürssen, both of Bergisch-Gladbach, all of Fed. Rep. of Germany

[73] Assignee: Bayer Aktiengesellschaft, Leverkusen, Fed. Rep. of Germany

[21] Appl. No.: 915,037

[22] Filed: Jul. 15, 1992

Related U.S. Application Data

[63] Continuation of Ser. No. 698,241, May 6, 1991, abandoned, which is a continuation of Ser. No. 514,785, Apr. 25, 1990, abandoned.

[30] Foreign Application Priority Data

May 18, 1989 [DE] Fed. Rep. of Germany ....... 3916208

[51] Int. Cl.$^5$ .................. A01N 43/653; C07D 249/12
[52] U.S. Cl. .................. 504/273; 548/263.4; 548/263.8; 504/219; 504/225; 504/235; 504/253; 504/249; 504/266; 504/269; 504/270; 504/271; 504/265; 504/262; 504/263; 504/248; 504/167; 504/168; 504/169; 504/170
[58] Field of Search ............... 71/92; 548/263.4, 263.8

[56] References Cited

U.S. PATENT DOCUMENTS

| | | | |
|---|---|---|---|
| 4,743,291 | 5/1988 | Maranetz | 548/263.8 |
| 4,931,084 | 6/1990 | Findeisen et al. | 548/263.8 |
| 5,061,311 | 10/1991 | Findeisen et al. | 548/263.8 |

FOREIGN PATENT DOCUMENTS

| | | | |
|---|---|---|---|
| 283876 | 9/1988 | European Pat. Off. | 71/92 |
| 919458 | 2/1963 | United Kingdom . | |

OTHER PUBLICATIONS

Fujino et al, "Copper Electroplating from , etc" CA 77:147067a (1972).

*Primary Examiner*—Patricia L. Morris
*Attorney, Agent, or Firm*—Sprung Horn Kramer & Woods

[57] ABSTRACT

Herbicidal substituted triazolones of the formula $$R^2-NH-C(=\!\!\!=\!\!N-R^1)-N-N(-N=\!\!\!=\!\!C(Y)-N(R^3)-R^4)-C(=\!\!X)$$  (I)

in which

R$^1$ represents hydrogen, alkyl, alkenyl, alkinyl, halogenoalkyl, halogenoalkenyl, halogenoalkinyl, alkoxyalkyl, alkoxy, cycloalkylalkyl or cycloalkyl, or represents in each case optionally substituted aralkyl or aryl, R$^2$ represents alkyl, alkenyl, alkinyl, halogenoalkyl, halogenoalkenyl, halogenoalkinyl, alkoxyalkyl, alkoxy, cycloalkyl or cycloalkylalkyl, or represents in each case optionally substituted aryl, aralkyl or heteroaryl, R$^3$ and R$^4$ independently of one another each represent hydrogen or an organic radical, or together with the nitrogen atom to which they are bonded represent an optionally substituted heterocycle, X represents oxygen or sulphur and Y represents oxygen or sulphur.

14 Claims, No Drawings

HERBICIDAL SUBSTITUTED TRIAZOLONES

This application is a continuation, of application Ser. No. 698,241, filed May 6, 1991, now abandoned, which is a continuation of application Ser. No. 514,785, filed Apr. 25, 1990, now abandoned.

The invention relates to new substituted triazolones, to several processes for their preparation, and to their use as herbicides.

It is known that certain substituted triazolones such as, for example, the compound 1-(cyclohexylaminocarbonyl)-3-dimethylamino-4-methyl-1, 2,4-triazolin-5-one, have herbicidal properties (cf., for example, European Patent 283,876).

However, the herbicidal activity of these previously known compounds against problem weeds, as well as their tolerance by important crop plants, is not entirely satisfactory in all fields of application.

New substituted triazolones of the general formula (I)

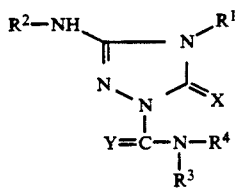

in which $R^1$ represents hydrogen, alkyl, alkenyl, alkinyl, halogenoalkyl, halogenoalkenyl, halogenoalkinyl, alkoxyalkyl, alkoxy, cycloalkylalkyl or cycloalkyl, or represents in each case optionally substituted aralkyl or aryl, $R^2$ represents alkyl, alkenyl, alkinyl, halogenoalkyl, halogenoalkenyl, halogenoalkinyl, alkoxyalkyl, alkoxy, cycloalkyl or cycloalkylalkyl, or represents in each case optionally substituted aryl, aralkyl or heteroaryl, $R^3$ and $R^4$ independently of one another each represent hydrogen, alkyl, alkenyl, alkinyl, halogenoalkyl, halogenoalkenyl, halogenoalkinyl, cyanoalkyl, hydroxyalkyl, alkoxyalkyl, alkylaminoalkyl, alkoximinoalkyl, alkoxycarbonylalkyl or alkoxycarbonylalkenyl, or represent in each case optionally substituted cycloalkyl, cycloalkylalkyl, cycloalkenyl or cycloalkenylalkyl, or represent optionally substituted heterocyclylalkyl, or represent in each case optionally substituted aralkyl, aroyl or aryl, or represent alkoxy, alkenyloxy, alkinyloxy, aralkyloxy or aryloxy, or together with the nitrogen atom to which they are bonded represent an optionally substituted heterocycle, X represents oxygen or sulphur and Y represents oxygen or sulphur, have been found.

Furthermore, it has been found that the new substituted triazolones of the general formula (I)

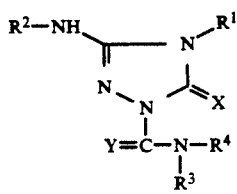

in which $R^1$, $R^2$, $R^3$, $R^4$, X and Y are as defined above, are obtained when a) 1-chloro-(thio)carbonyltriazolones of the formula (II)

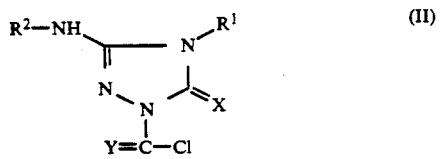

in which $R^1$, $R^2$, X and Y are as defined above, are reacted with amines of the formula (III)

in which $R^3$ and $R^4$ are as defined above, if appropriate in the presence of a diluent and if appropriate in the presence of an acid-binding agent, or b) in the event that $R^3$ in formula (I) represents hydrogen, when triazolones which are unsubstituted in the 1-position, of the formula (IV)

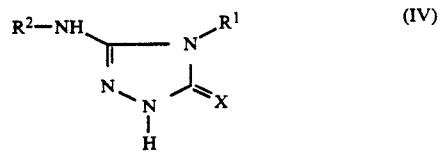

in which $R^1$, $R^2$ and X are as defined above, are reacted with iso(thio)cyanates of the formula (V)

in which $R^4$ and Y are as defined above, if appropriate in the presence of a diluent and if appropriate in the presence of a reaction auxiliary.

Finally, it has been found that the new substituted triazolones of the general formula (I) have herbicidal properties.

Surprisingly, the substituted triazolones of the general formula (I) according to the invention have a considerably more powerful herbicidal potency against problem weeds than the substituted triazolones which are known from the prior art, such as, for example, the compound 1-(cyclohexylaminocarbonyl)-3-dimethylamino-4-methyl-1, 2,4-triazolin-5-one, which are compounds of a similar chemical structure and similar type of action.

Formula (I) provides a general definition of the substituted triazolones according to the invention. Preferred compounds of the formula (I) are those in which $R^1$ represents hydrogen, or represents in each case straight-chain or branched alkyl having 1 to 8 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, halogenoalkinyl having 2 to 8 carbon atoms and 1 to 13 identical or different halogen atoms, alkoxyalkyl or alkoxy, each of which has 1 to 6 carbon atoms in the individual alkyl moieties, or represents cycloalkylalkyl or cycloalkyl, each of which has 3 to 7 carbon atoms in the cycloalkyl moiety and, if appropriate, 1 to 6 carbon atoms in the straight-chain or branched alkyl moiety, or represents aralkyl or aryl, each of which has 6 to 10 carbon atoms in the aryl moiety and, if appropriate, 1 to 6 carbon atoms in the straight-chain or branched alkyl moiety and each of which is optionally monosubstituted or polysubstituted by identical or different substituents, suitable aryl substituents being: halogen, cyano, nitro, and in each case straight-chain or branched alkyl, alkoxy, alkylthio, halogenoalkyl, halogenoalkoxy or halogenoalkylthio, each of which has 1 to 4 carbon atoms and, if appropriate, 1 to 9 identical or different halogen atoms, $R^2$ represents in each case straight-chain or branched alkyl having 1 to 8 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl or halogenoalkinyl, each of which has 2 to 8 carbon atoms and 1 to 15, or 13, identical or different halogen atoms, alkoxyalkyl or alkoxy, each of which has 1 to 6 carbon atoms in the individual alkyl moieties, or represents cycloalkyl having 3 to 7 carbon atoms, or represents cycloalkylalkyl having 3 to 7 carbon atoms in the cycloalkyl moiety and 1 to 6 carbon atoms in the alkyl moiety, or represents aralkyl which has 6 to 10 carbon atoms in the aryl moiety and 1 to 6 carbon atoms in the alkyl moiety and which is optionally monosubstituted or polysubstituted by identical or different substituents, aryl which has 6 to 10 carbon atoms and which is optionally monosubstituted or polysubstituted by identical or different substituents, or heteroaryl which has 2 to 9 carbon atoms and 1 to 3 heteroatoms, in particular nitrogen, oxygen and/or sulphur, and which is optionally monosubstituted or polysubstituted by identical or different substituents, suitable substituents in the aryl or heteroaryl moiety in each case being: halogen, cyano, nitro and in each case straight-chain or branched alkyl, alkoxy, alkylthio, halogenoalkyl, halogenoalkoxy or halogenoalkylthio, each of which has 1 to 4 carbon atoms and if appropriate 1 to 9 identical or different halogen atoms, $R^3$ and $R^4$ independently of one another each represents hydrogen, or represent in each case straight-chain or branched alkyl having 1 to 18 carbon atoms, alkenyl having 2 to 8 carbon atoms, alkinyl having 2 to 8 carbon atoms, halogenoalkyl having 1 to 8 carbon atoms and 1 to 17 identical or different halogen atoms, halogenoalkenyl or halogenoalkinyl, each of which has 2 to 8 carbon atoms and 1 to 15, or 13, identical or different halogen atoms, cyanoalkyl having 1 to 8 carbon atoms, hydroxyalkyl having 1 to 8 carbon atoms and 1 to 6 hydroxyl groups, alkoxyalkyl, alkoxycarbonylalkyl or alkoxycarbonylalkenyl, each of which has up to 6 carbon atoms in the individual alkyl or alkenyl moieties, or represent alkylaminoalkyl, dialkylaminoalkyl or alkoximinoalkyl, each of which has 1 to 8 carbon atoms in the individual alkyl moieties, or represent cycloalkyl, cycloalkylalkyl, cycloalkenyl or cycloalkenylalkyl, each of which has 3 to 8 carbon atoms in the cycloalkyl or cycloalkenyl moiety and if appropriate 1 to 6 carbon atoms in the alkyl moiety and each of which is optionally monosubstituted or polysubstituted by identical or different substituents, suitable substituents in each case being: halogen, cyano and in each case straight-chain or branched alkyl or halogenoalkyl, each of which has 1 to 4 carbon atoms and if appropriate 1 to 9 identical or different halogen atoms or in each case double-linked alkanediyl or alkenediyl, each of which has up to 4 carbon atoms; $R^3$ and $R^4$ furthermore independently of one another represent heterocyclylalkyl which has 1 to 6 carbon atoms in the straight-chain or branched alkyl moiety and 1 to 9 carbon atoms and also 1 to 3 heteroatoms—in particular nitrogen, oxygen and/or sulphur—in the heterocyclyl moiety and which is optionally monosubstituted or polysubstituted in the heterocyclyl moiety by identical or different substituents, suitable substituents being: halogen, cyano, nitro, and in each case straight-chain or branched alkyl, alkoxy, alkylthio, halogenoalkyl, halogenoalkoxy, halogenoalkylthio or alkoxycarbonyl, each of which has 1 to 5 carbon atoms and if appropriate 1 to 9 identical or different halogen atoms; $R^3$ and $R^4$ furthermore independently of one another represent in each case straight-chain or branched alkoxy having 1 to 8 carbon atoms, alkenyloxy having 2 to 8 carbon atoms or alkinyloxy having 2 to 8 carbon atoms, and finally represent aralkyl, aralkyloxy, aryloxy, aroyl or aryl, each of which has 6 to 10 carbon atoms in the aryl moiety and if appropriate 1 to 6 carbon atoms in the alkyl moiety and each of which is optionally monosubstituted or polysubstituted by identical or different substituents, suitable aryl substituents in each case being: halogen, cyano, nitro, hydroxyl, in each case straight-chain or branched alkyl, alkoxy, alkylthio, halogenoalkyl, halogenoalkoxy, halogenoalkylthio, alkylsulphinyl, alkylsulphonyl, halogenoalkylsulphinyl, halogenoalkylsulphonyl, alkanoyl or alkoxycarbonyl, each of which has 1 to 6 carbon atoms and if appropriate 1 to 9 identical or different halogen atoms, cycloalkyl having 3 to 6 carbon atoms or phenoxy, and, if appropriate, suitable alkyl substituents being: halogen or cyano, or $R^3$ and $R^4$ together with the nitrogen atom to which they are bonded represent a five- to ten-membered heterocycle which, if appropriate, can contain 1 to 2 further heteroatoms, in particular nitrogen, oxygen and/or sulphur, and which is optionally monosubstituted or polysubstituted by identical or different substituents, suitable substituents being: halogen and in each case straight-chain or branched alkyl or halogenoalkyl, each of which have 1 to 4 carbon atoms and if appropriate 1 to 9 identical or different halogen atoms and also 1 to 2 oxo or thiono groups, X represents oxygen or sulphur and Y represents oxygen or sulphur.

Particularly preferred compounds of the formula (I) are those in which $R^1$ represents hydrogen, methyl, ethyl, n- or i-propyl, n-, i-, s- or t-butyl, n- or i-pentyl or n- or i-hexyl, or represents allyl, propargyl, methoxy, ethoxy or methoxymethyl, or represents straight-chain or branched halogenoalkyl having 1 to 4 carbon atoms and 1 to 9 identical or different halogen atoms, in particular fluorine, chlorine or bromine, or represents cyclopentyl, cyclohexyl, cyclopropyl, cyclopropylmethyl, cyclohexylmethyl or cyclohexylethyl, or represents benzyl or phenyl, each of which is optionally monosubstituted to trisubstituted by identical or different substituents, suitable substituents being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio, R² represents methyl, ethyl, n- or i-propyl, n-, i-, s- or t-butyl, n- or i-pentyl, allyl or propargyl, or represents in each case straight-chain or branched halogenoalkyl having 1 to 4 carbon atoms, halogenoalkenyl having 3 to 6 carbon atoms or halogenoalkinyl having 3 to 6 carbon atoms and in each case 1 to 9 identical or different halogen atoms, or represents methoxymethyl, methoxyethyl, methoxy or ethoxy, or represents cyclopropyl, cyclopropylmethyl, cyclopentyl, cyclohexyl, cyclohexylmethyl, cyclohexylethyl or cyclopentylmethyl, or represents benzyl, phenylethyl or phenyl, each of which is optionally monosubstituted to trisubstituted by identical or different substituents, suitable substituents in each case being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio, R³ and R⁴ independently of one another each represent hydrogen, methyl, ethyl, n- or i-propyl, n-, i-, s- or t-butyl, n- or i-pentyl, n- or i-hexyl, n- or i-heptyl, n- or i-octyl, n- or i-nonyl, n- or i-decyl, n- or i-dodecyl, or represent allyl, n- or i-butenyl, n- or i-pentenyl, n- or i-hexenyl, propargyl, n- or i-butinyl, n- or i-pentinyl, n- or i-hexinyl, or represent straight-chain or branched halogenoalkyl having 1 to 6 carbon atoms and 1 to 9 identical or different halogen atoms, in particular fluorine, chlorine or bromine, or represent in each case straight-chain or branched halogenoalkenyl or halogenoalkinyl, each of which has 3 to 8 carbon atoms and 1 to 3 halogen atoms, in particular fluorine or chlorine, or represent in each case straight-chain or branched cyanoalkyl having 1 to 6 carbon atoms in the alkyl moiety, hydroxyalkyl having 1 to 6 carbon atoms and 1 to 3 hydroxyl groups, alkoxyalkyl, alkoxycarbonylalkyl or alkoxycarbonylalkenyl, alkylaminoalkyl or dialkylaminoalkyl, each of which has up to 4 carbon atoms in the individual alkyl or alkenyl moieties, or represent in each case optionally straight-chain or branched methoximinoalkyl or ethoximinoalkyl, each of which has 1 to 5 carbon atoms in the alkyl moiety, or represent cyclopropyl, cyclopropylmethyl, cyclopropylethyl, cyclopentyl, cyclohexyl, cycloheptyl, cyclooctyl, cyclohexylmethyl, cyclohexylethyl, cyclohexenyl or cyclohexenylmethyl, each of which is optionally monosubstituted to trisubstituted by identical or different substituents, suitable substituents in each case being: fluorine, chlorine, bromine, methyl, ethyl, n- or i-propyl, n-, i-, s- or t-butyl, cyano, methanediyl, ethanediyl, butanediyl or butadienediyl; R³ and R⁴ furthermore independently of one another represent heterocyclylmethyl, heterocyclylpropyl, heterocyclylethyl or heterocyclylbutyl, each of which is optionally monosubstituted to trisubstituted in the heterocyclyl moiety by identical or different substituents, suitable substituents being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy or trifluoromethylthio, and suitable heterocycles in each case being:

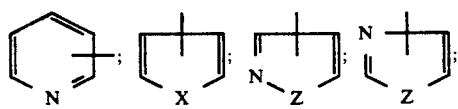

-continued

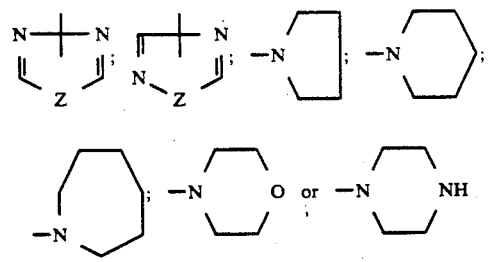

where Z in each case represents oxygen or sulphur; R³ and R⁴ furthermore independently of one another represent in each case straight-chain or branched alkoxy having 1 to 6 carbon atoms, alkenyloxy having 3 to 6 carbon atoms or alkinyloxy having 3 to 6 carbon atoms, or represent benzyl, phenylethyl, phenylpropyl, phenylbutyl, phenylpentyl, phenylhexyl, phenylheptyl, phenylcyanomethyl, phenylcyanoethyl, phenylcyanopropyl, benzyloxy, phenylethyloxy, phenoxy, benzoyl, phenyl or naphthyl, each of which is optionally monosubstituted to trisubstituted by identical or different substituents, suitable phenyl substituents in each case being: fluorine, chlorine, bromine, hydroxyl, cyano, nitro, methyl, ethyl, n- or i-propyl, n-, i-, s- or t-butyl, methoxy, ethoxy, methylthio, trifluoromethyl, trifluoromethoxy, trifluoromethylthio, trifluoromethylsulphinyl, trifluoromethylsulphonyl, methylsulphinyl, methylsulphonyl, acetyl, propionyl, methoxycarbonyl, ethoxycarbonyl, cyclohexyl or phenoxy; or R³ and R⁴ together with the nitrogen atom to which they are bonded represent a heterocycle of the formula

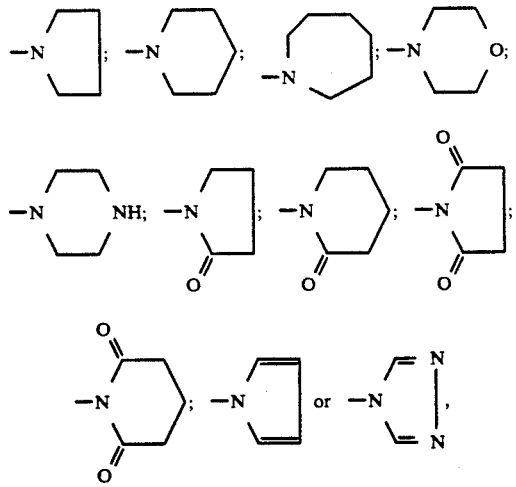

optionally monosubstituted to trisubstituted by identical or different substituents, suitable substituents in each case being: methyl, ethyl, n- or i-propyl, chlorine or trifluoromethyl, X represents oxygen or sulphur and Y represents oxygen or sulphur.

If, for example, 1-chlorocarbonyl-3-methylamino-4-methyl-1,2,4-triazolin-5-one and allyl amine are used as the starting substances, the course of the reaction of process (a) according to the invention may be represented by the following equation:

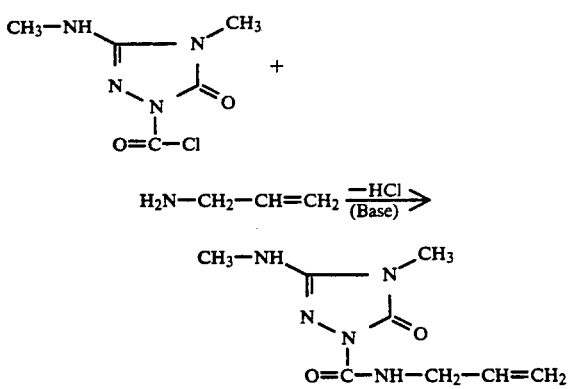

If, for example, 3-ethylamino-4-methyl-1H-1, 2,4-triazolin-5-one and isopropyl isocyanate are used as the starting substances, the course of the reaction of process (b) according to the invention may be represented by the following equation:

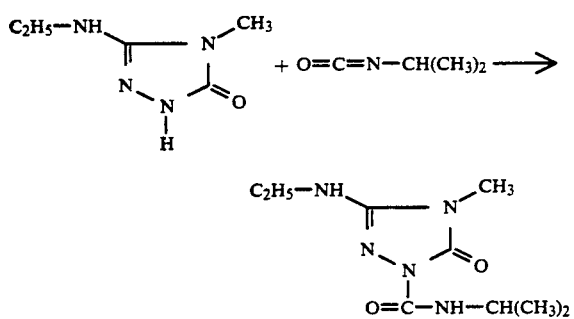

Formula (II) provides a general definition of the chloro(thio)carbonyltriazolones required as starting substances for carrying out process (a) according to the invention. In this formula (II), $R^1$, $R^2$, X and Y preferably represent those radicals which have already been mentioned in connection with the description of the substances of the formula (I) according to the invention as being preferred for these substituents.

The chloro(thio)carbonyltriazolones of the formula (II) were hitherto unknown.

They are obtained when triazolones which are unsubstituted in the 1-position, of the formula (IV)

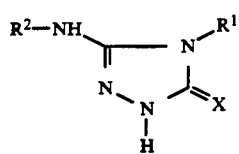 (IV)

in which
$R^1$, $R^2$ and X are as defined above, are reacted with (thio)phosgene of the formula (VI)

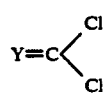 (VI)

in which
Y is as defined above, if appropriate in the presence of a diluent, such as, for example, toluene, chlorobenzene or acetonitrile, and if appropriate in the presence of an acid-binding agent, such as, for example, triethylamine, at temperatures between +20° C. and +150° C.

Formula (III) provides a general definition of the amines furthermore required as starting substances for carrying out process (a) according to the invention. In this formula (III), $R^3$ and $R^4$ preferably represent those radicals which have already been mentioned in connection with the description of the substances of the formula (I) according to the invention as being preferred for these substituents.

The amines of the formula (III) are generally known compounds of organic chemistry.

Formula (IV) provides a general definition of the triazolones which are unsubstituted in the 1-position and which are required as starting substances for carrying out process (b) according to the invention and for synthesizing the precursors of the formula (II). In this formula (IV), $R^1$, $R^2$ and X preferably represent those radicals which have already been mentioned in connection with the description of the substances of the formula (I) according to the invention as being preferred for these substituents.

The triazolones which are unsubstituted in the 1-position, of the formula (IV), are known or can be obtained in analogy to known processes (cf., for example, European Patent 283,876; Arch. Pharm. 303, 263–267 [1970]; Arch. Pharm. 307, 509–516 [1974]; J. Org. Chem. 34, 1808–1816 [1969]; Chem. Ber. 107, 454–459 [1974]; J. Heterocycl. Chem. 15, 377–384 [1978]; Pharmazie 29, 20–25 [1974]; Indian J. Chem. 8, 391–394 [1970]; Indian J. Chem. 6, 287–293 [1968]; Japanese Patent 46/37,646; Japanese Patent 62/2,248 Japanese Patent 62/153,850; DE 2,714,880; DE 2,716,707; Indian J. Chem. Sect. B 21B, 321–324 [1982]; Helv. Chim. Acta 63, 841–859 [1980]; DE 2,145,414; J. Chem. Soc. C 1967, 24⁻1–2472; J. Chem. Soc. C 1967, 746–751; J. Chem. Soc. C 1968, 1375–1380; J. Chem. Soc. C 1967, 742–746; GB 1,049,111; Arch. Pharm. 306, 659–664 [1973]; Farmacia 15, 415–419 [1967] and the Preparation Examples).

The compounds of the formula (IV) in which (α) X represents oxygen and $R^1$ and $R^2$ represent methyl, or in which (β) X represents oxygen or sulphur and $R^1$ represents methyl and, simultaneously, $R^2$ represents ethyl, or $R^1$ represents ethyl and, simultaneously, $R^2$ represents methyl, or $R^1$ and $R^2$ represent ethyl, are new.

The new and known compounds of the formula (IV) are obtained, for example, when aminoguanidinium hydrochlorides (VIIb)

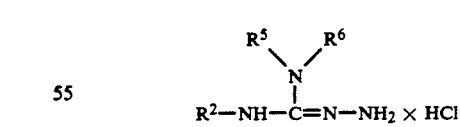

in which
$R^5$ and $R^6$ represent alkyl, in particular methyl or ethyl, and
$R^2$ is as defined above, are reacted with iso(thio)cyanates of the formula (X)

$R^1$—N=C=X (X)

in which
$R^1$ and X are as defined above, if appropriate in the presence of a diluent such as, for example, toluene, chlorobenzene or acetonitrile, and if appropriate in the presence of an acid-binding agent, such as, for example, potassium carbonate or triethylamine, at temperatures between 20° and 150° C., or when 3alkylthiotriazolones of the formula (XI)

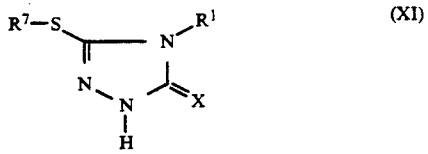

in which

R[7] represents alkyl, in particular methyl or ethyl, and R[1] and X are as defined above, are reacted with amines of the formula (XII)

in which

R[2] is as defined above, if appropriate in the presence of a diluent such as, for example, ethanol or acetonitrile, at temperatures between 50° and 300° C. in pressure ranges between atmospheric pressure and 300 bar.

Aminoguanidinium hydrochlorides of the formula (VIIb) are known or can be obtained in analogy to known processes (cf., for example, European Patent 283,876; J. Org. Chem. 19, 1807 [1954]; Bull. Soc. Chim. France 1975, 1649; U.S. Pat. No. 2,845,458).

Iso(thio)cyanates of the formula (X) are generally known compounds of organic chemistry.

3-alkylthiotriazolones of the formula (XI) are likewise known (cf., for example, European Patent 283,876; DE 2,527,676; DE 2,250,572; U.S. Pat. No. 4,098,896; U.S. Pat. No. 4,110,332; U.S. Pat. No. 4,530,898; J. Chem. Soc. C 1967, 746-751).

Amines of the formula (XII) are generally known compounds of organic chemistry.

Formula (V) provides a general definition of the iso(thio)cyanates furthermore required as starting substances for carrying out process (b) according to the invention. In this formula (V), R[4] and Y preferably represent those radicals which have already been mentioned in connection with the description of the substances of the formula (I) according to the invention as being preferred for these substituents.

The iso(thio)cyanates are generally known compounds of organic chemistry (cf., for example, Saul Patai, "The Chemistry of Cyanates and their Thioderivates" J. Wiley & Sons, New York 1977).

Preferred suitable diluents for carrying out process (a) according to the invention are inert organic solvents.

These include, in particular, aliphatic, alicyclic or aromatic, optionally halogenated hydrocarbons, such as, for example, benzine, ligroin, benzene, toluene, xylene, chlorobenzene, petroleum ether, pentane, hexane, heptane, cyclohexane, dichloromethane, chloroform and carbon tetrachloride, ethers, such as diethyl ether, dioxane, tetrahydrofuran, ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, or bases, such as pyridine.

If appropriate, process (a) according to the invention is carried out in the presence of a suitable acid-binding agent.

Suitable acid-binding agents are all customary inorganic or organic bases. These include, for example, alkali metal hydroxides, such as sodium hydroxide or potassium hydroxide, alkali metal carbonates, such as sodium carbonate, potassium carbonate or sodium hydrogen carbonate, and tertiary amines, such as triethylamine, N,N-dimethylaniline, pyridine, N,N-dimethylaminopyridine, diazabicyclooctane (DABCO), diazabicyclononene (DBN) or diazobicycloundecene (DBU).

It is also possible to employ the amine of the formula (III), which is used as a reactant, in appropriate excess to act simultaneously as an acid-binding agent.

When carrying out process (a) according to the invention, the reaction temperatures can be varied within a substantial range. In general, the process is carried out at temperatures between 0° C. and +150° C., preferably at temperatures between +10° C. and +80° C.

Process (a) according to the invention is customarily carried out under atmospheric pressure. However, it is also possible to carry out the process under increased pressure.

For carrying out process (a) according to the invention, 1.0 to 5.0 moles, preferably 1.0 to 2.5 moles, of the amine of the formula (III) and if appropriate 1.0 to 2.5 moles of acid-binding agent are generally employed per mole of 1-chlor-(thio)carbonyltriazolone of the formula (II). The reaction is carried out and the reaction products are worked up and isolated in analogy to generally known processes.

Suitable diluents for carrying out process (b) according to the invention are likewise inert organic solvents. The diluents which have been mentioned in process (a) are preferably used.

If appropriate, process (b) according to the invention can be carried out in the presence of a basic reaction auxiliary. Suitable basic reaction auxiliaries are all customary inorganic and organic bases. Tertiary amines, such as triethylamine, N,N-dimethylaniline, pyridine, N,N-dimethylaminopyridine, diazabicyclooctane (DABCO), diazabicyclononene (DBN) or diazabicycloundecene (DBU) are preferably used.

However, it is not absolutely necessary to add such catalysts.

When carrying out process (b) according to the invention, the reaction temperatures can be varied within a substantial range. In general, the process is carried out at temperatures between 0° C. and +150° C., preferably at temperatures between +40° C. and +120° C.

Process (b) according to the invention is customarily carried out under atmospheric pressure. However, it is also possible to carry out the process under increased pressure, in particular in the case of gaseous starting compounds.

For carrying out process (b) according to the invention, 1.0 to 5.0 moles, preferably 1.0 to 2.5 moles, of iso(thio)cyanate of the formula (V) and if appropriate 1.0 to 2.5 moles of reaction auxiliary are generally employed per mole of triazolone which is unsubstituted in the 1-position, of the formula (IV). The reaction is carried out and the reaction products are worked up and isolated in analogy to generally known processes.

The active compounds according to the invention can be used as defoliants, desiccants, agents for destroying broad-leaved plants and, especially, as weedkillers.

By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Iponioea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

In this context, the active compounds of the formula (I) according to the invention can be employed with particularly good success for combating dicotyledon weeds, in particular in monocotyledon cultures, such as, for example, maize.

Moreover, the active compounds according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amount of active compound applied to the plants or their environment, and the way in which the compounds are applied. In each case, growth regulators are intended to influence the crop plants in the particular manner desired.

Under the influence of growth regulators, the amount of leaf on plants can be controlled so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to reduce the transpiration of the plants before they are transplanted.

In appropriate application rates, the active compounds according to the invention also show a fungicidal activity and can be employed, for example, for combating fungal diseases in cereal and rice growing, such as, for example, against the pathogen causing mildew on cereals (Erysiphe graminis) or against the pathogen causing rice blast disease (Pyricularia oryzae) or for combating fungal diseases in fruit and vegetable growing, such as, for example, against the pathogen of apple scab (Venturia inaequalis), or against Cercospora species. In this field of application, the active compounds according to the invention show not only good protective properties, but also systemic properties.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and ULV cold mist and warm mist formulations.

These formulations are produced in a known manner, for example by mixing the active compounds with extenders, that is, liquid solvents, liquefied gases under pressure and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogen hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2, 2-dimethylpropyl)-1,3,5-triazine-2,4(1H, 3H)-dione (AMETHYDIONE) or N-(2-benzothiazolyl)-N,N'-dimethylurea (METABENZTHIAZURON) for combating weeds in cereals; 4-amino-3-methyl-6-phenyl-1,2, 4-triazin-5(4H)-one (METAMITRON) for combating weeds in sugar beets and 4-amino-6-(1,1-dimethylethyl)-3-methylthio-1, 2,4-triazin-5(4H)-one (METRIBUZIN) for combating weeds in soy beans. Mixtures with 2,4-dichlorophenoxyacetic acid (2,4-D); 4-(2,4-dichlorophenoxy)-butyric acid (2,4-DB); 2,4dichlorophenoxypropionic acid (2,4-DP); 2-chloro-4-ethylamino-6-isopropylamino-1,3, 5-triazine(ATRAZINE); 3-isopropyl-2,1, 3-benzothiadiazin-4-one 2,2-dioxide (BENTAZONE); methyl 5-(2, 4-dichlorophenoxy)-2-nitrobenzoate (BIFENOX); 3,5-dibromo-4-hydroxy-benzonitrile (BROMOXYNIL); 2-chloro-N{[(4-methoxy-6-methyl-1, 3,5-triazin-2-yl)-amino]-carbonyl}benzenesulphonamide (CHLORSULFURON); N,N-dimethyl-N'-(3-chloro-4-methylphenyl)-urea (CHLORTOLURON); 2-chloro-4-ethylamino-6-(3-cyanopropylamino) -1,3,5-triazine (CYANAZIN); 2-[4-(2, 4-dichlorophenoxy)-phenoxy]-propionic acid, its methyl ester or its ethyl ester (DICLOFOP); 4-amino-6-t-butyl-3-ethylthio-1,24-thiazin-5(44)-one (ETHIOZIN); 2-{4-[(6-chloro-2-benzoxazolyl)-oxy]-phenoxy}-propanoic acid, its methyl ester or its ethyl ester (FENOXAPROP); [(4-amino-3, 5-dichloro-6-fluoro-2-pyridinyl)-oxy]-acetic acid or its 1-methylheptyl ester (FLUROXYPYR); methyl 2-[4, 5-dihydro-4-methyl-4-(1-methylethyl)-5-oxo-1H-imidazol-2-yl]-4(5)-methylbenzoate (IMAZAMETHABENZ); 3,5-diiodo-4-hydroxybenzonitrile (IOXYNIL); N,N-dimethyl-N'-(4-isopropylphenyl)-urea (ISOPROTURON); (2-methyl-4-chlorophenoxy)-acetic acid (MCPA); (4-chloro-2-methylphenoxy)-propionic acid (MCPP); N-methyl-2-(1, 3-benzothiazol-2-yloxy)-acetanilide (MEFENACET); 2-{[[((4-methoxy-6-methyl-1, 3,5-triazin-2-yl)amino)-carbonyl]-amino]-sulphonyl}-benzoic acid or its methyl ester (METSULFURON); N-(1-ethylpropyl)-3, 4-dimethyl-2,6-dinitroaniline (PENDIMETHALIN); 0-(6-chloro-3-phenyl-pyridazin-4-yl) S-octyl thiocarbonate (PYRIDATE); 4-ethylamino-2-t-butylamino-6-methylthio-striazine (TERBUTRYNE); methyl 3-[[[[(4-methoxy-6-methyl-1,3,5-triazin-2-yl)-amino]-carbonyl]-amino]-sulphonyl]-thiophene-2-carboxylate (THIAMETURON) and S-2,3,3-trichloroallyl N,N-diisopropylthiolcarbamate (TRIALLATE) are also possible. Surprisingly, some mixtures also show synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

PREPARATION EXAMPLES

Example 1

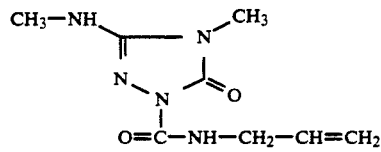

Process b 4.2 g (0.05 mol) of allyl isocyanate and 3 drops of diazabicycloundecene (DBU) are added to 6.4 g (0.05 mol) of 3-methylamino-4-methyl-(1H)-1,2, 4-triazolin-5-one in 150 ml of acetonitrile, during which process the temperature of the reaction mixture rises to 30° C. The mixture is subsequently stirred for 30 minutes at reflux temperature and evaporated in vacuo, and the residue is recrystallized from ethyl acetate.

This gives 7.9 g (75% of theory) of 1-allylaminocarbonyl-3-methylamino-4-methyl-1,2, 4-triazolin-5-one of melting point 136°-137° C.

Example 2

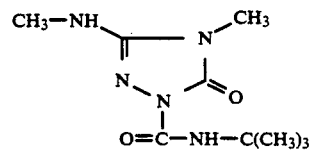

Process b 4.95 g (0.05 mol) of t-butyl isocyanate and 3 drops of diazabicycloundecene (DBU) are added to 6.4 g (0.05 mol) of 3-methylamino-4-methyl-(1H)-1, 2,4-triazolin-5-one in 150 ml of acetonitrile, the mixture is subsequently stirred for 30 minutes at the reflux temperature and filtered, and the filtrate is evaporated in vacuo.

This gives 6.5 g (57% of theory) of 1-t-butyl-aminocarbonyl-3-methylamino-4-methyl-1, 2,4-triazolin-5-one of melting point 210° C. (decomposition).

Example 3

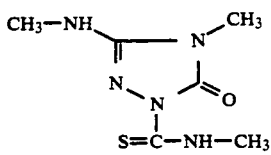

Process b 3.65 g (0.05 mol) of methyl isothiocyanate and 3 drops of diazabicycloundecene (DBU) are added to 6.4 g (0.05 mol) of 3-methylamino-4-methyl-(1H)-1, 2,4-triazolin-5-one in 150 ml of acetonitrile, the mixture is subsequently stirred for 30 minutes at 40° C. to 50° C. and, after this, another 30 minutes at 70° C. to 80° C. and then evaporated in vacuo, and the residue is recrystallized from ethyl acetate/acetonitrile (3:1).

This gives 4.95 g (49% of theory) of 1-methylamino-thiocarbonyl-3-methylamino-4-methyl-1, 2,4-triazolin-5-one of melting point 161°-163° C.

Example 4

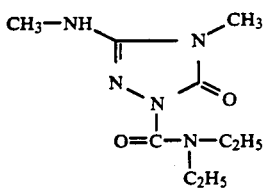

Process a 8.83 g (0.12 mol) of diethylamine are added dropwise with stirring to 11.4 g (0.06 mol) of 1-chlorocarbonyl-3-methylamino-4-methyl-(1,2, 4)-triazolin-5-one in 200 ml of acetonitrile in such a way that the temperature of the reaction mixture does not exceed 40° C. When the addition is complete, stirring is continued for 2 hours at room temperature, the mixture is filtered, and the filtrate is evaporated in vacuo, the residue is taken up in 150 ml of acetone, and the mixture is again filtered, and the filtrate is again evaporated in vacuo.

This gives 12.2 g (90% of theory) of 1-diethylaminocarbonyl-3-methylamino-4-methyl-1, 2,4-triazolin-5-one of melting point 83° C. to 85° C.

Example 5

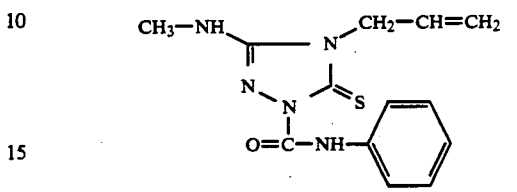

Process b 5.95 g (0.05 mol) of phenyl isocyanate are added to 8.5 g (0.05 mol) of 3-methylamino-4-allyl-(1H)-1,2, 4-triazolin-5-thione in 150 ml of acetonitrile, the mixture is subsequently stirred for 1 hour at the reflux temperature then evaporated in vacuo, and the residue is recrystallized from toluene/cyclohexane (1:1).

This gives 8.7 g (60% of theory) of 1-phenylaminocarbonyl-3-methylamino-4-allyl-1,2, 4-triazolin-5-thione of melting point 132°-133° C.

The following substituted triazolones of the general formula (I)

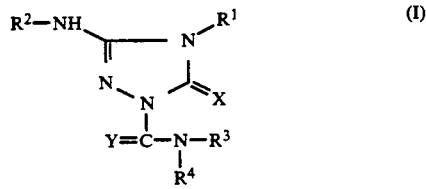

are obtained in a corresponding manner and following the general preparation instructions:

TABLE 1

| Example No | R¹ | R² | —N—R³<br>\|<br>R⁴ | X | Y | Melting point/°C. |
|---|---|---|---|---|---|---|
| 6 | CH₃ | CH₃ | —NH—CH₂—C(CH₃)₃ | O | O | 208–209 |
| 7 | CH₃ | CH₃ | —NH—⟨H⟩ | O | O | 172–173 |
| 8 | CH₃ | CH₃ | —NH—CH₃ | O | O | 226–227 |
| 9 | CH₃ | CH₃ | —NH—C₂H₅ | O | O | 182–183 |
| 10 | CH₃ | CH₃ | —NH—(CH₂)₂—CH₃ | O | O | 124–125 |
| 11 | CH₃ | CH₃ | —NH—CH(CH₃)₂ | O | O | 160–162 |
| 12 | CH₃ | CH₃ | —NH—C(CH₃)(CH₃)—CH₂Cl | O | O | 221 |
| 13 | CH₂=CH—CH₂— | CH₃ | —NH—CH₂—C(CH₃)₃ | O | O | 182–183 |
| 14 | CH₂=CH—CH₂— | CH₃ | —NH—⟨H⟩ | S | O | 147 |

TABLE 1-continued

| Example No | R¹ | R² | -N(R³)(R⁴) | X | Y | Melting point/°C |
|---|---|---|---|---|---|---|
| 15 | CH₃ | CH₃ | -NH-C₆H₅ | O | O | 104 |
| 16 | CH₃ | CH₃ | -NH-CH₂-CH=CH₂ | O | S | 161-162 |
| 17 | CH₂=CH-CH₂- | CH₃ | -NH-CH₃ | S | O | 144 |
| 18 | CH₂=CH-CH₂- | CH₃ | -NH-(CH₂)₂-CH₃ | S | O | 117 |
| 19 | CH₂=CH-CH₂- | CH₃ | -NH-CH(CH₃)₂ | S | O | 126-127 |
| 20 | CH₃ | CH₃ | -NH-(CH₂)₃-CH₃ | O | O | 110 |
| 21 | CH₃ | CH₃ | -NH-CH₂-C(CH₃)₃ | S | O | 203 |
| 22 | CH₃ | CH₃ | -NH-cyclopropyl | O | O | 191 |
| 23 | CH₃ | CH₃ | -NH-cyclohexyl | S | O | 180-181 |
| 24 | CH₃ | CH₃ | -NH-cyclopropyl | S | O | 187 |
| 25 | CH₃ | CH₃ | -NH-(CH₂)₂-CH₃ | S | O | 157-159 |
| 26 | CH₃ | CH₃ | -NH-C(CH₃)₂-CH₂Cl | S | O | 196 |
| 27 | CH₃ | CH₃ | -NH-C(CH₃)(CH₂Cl)₂ | S | O | 183-185 |
| 28 | CH₃ | CH₃ | -NH-(2,6-Cl₂-4-CF₃-C₆H₂) | O | O | 231-232 |
| 29 | CH₃ | CH₃ | -NH-CH(CH₃)-C₂H₅ | O | O | 181-182 |
| 30 | CH₃ | CH₃ | -NH-CH₂-CH₂Cl | O | O | 215 |
| 31 | CH₃ | CH₃ | -NH-CH₂-COOC₂H₅ | O | O | 163-164 |
| 32 | CH₃ | CH₃ | -NH-CH(CH₃)-C₆H₅ | O | O | 165 |
| 33 | CH₃ | CH₃ | -NH-C(CH₃)(CH₂F)₂ | O | O | 196-197 |
| 34 | CH₃ | CH₃ | -NH-C(CH₃)₂-CF₃ | O | O | 259-262 |

TABLE 1-continued

| Example No | $R^1$ | $R^2$ | $-N(R^3)(R^4)$ | X | Y | Melting point/°C |
|---|---|---|---|---|---|---|
| 35 | $CH_3$ | $CH_3$ | $-NH-C(CN)(C_2H_5)(CH_3)$ | O | O | 22-224 |
| 36 | $CH_3$ | $CH_3$ | $-NH-C(CN)(CH_3)$-(3-Cl-C$_6$H$_4$) | O | O | 165 |
| 37 | $CH_3$ | $CH_3$ | $-NH-CH_2-CH_2-OC_2H_5$ | O | O | 115 |
| 38 | $CH_3$ | $CH_3$ | $-NH-C(CH_2Cl)_2(CH_3)$ | O | O | 215 |
| 39 | $CH_3$ | $CH_3$ | $-NH-C(CH_3)_2-CHCl_2$ | O | O | 216 |
| 40 | $CH_3$ | $CH_3$ | $-NH-C(CH_3)_2$-C$_6$H$_5$ | O | O | 169-170 |
| 41 | $CH_3$ | $CH_3$ | $-N$-(3-Cl-C$_6$H$_4$) | O | O | 221-224 |
| 42 | $CH_3$ | $CH_3$ | $-NH$-(3-CF$_3$-C$_6$H$_4$) | O | O | 180-182 |
| 43 | $C_2H_5$ | $CH_3$ | $-NH-CH_2-C(CH_3)_3$ | O | O | 181-182 |
| 44 | $C_2H_5$ | $CH_3$ | $-NH$-cyclohexyl | O | O | 145-146 |
| 45 | $C_2H_5$ | $CH_3$ | $-NH$-(3-Cl-C$_6$H$_4$) | O | O | 160-162 |
| 46 | $C_2H_5$ | $CH_3$ | $-NH-CH(CH_3)_2$ | O | O | 144-146 |
| 47 | $CH_3$ | $CH_3$ | $-NH$-(1-methylcyclohexyl) | O | O | 238-239 |
| 48 | $CH_3$ | $CH_3$ | $-NH-C(CH_3)_2-C\equiv CH$ | O | O | 200 (decomp.) |

TABLE 1-continued

| Example No | R¹ | R² | $-N(R^3)(R^4)$ | X | Y | Melting point/°C |
|---|---|---|---|---|---|---|
| 49 | CH₃ | CH₃ | —NH—(1-naphthyl) | O | O | 208–211 |
| 50 | CH₃ | CH₃ | —NH—CH(CH₃)—CH₂Cl | O | O | 155–156 |
| 51 | CH₃ | CH₃ | —NH—CH(CH₃)—CH₂Cl | S | O | 180 |
| 52 | CH₃ | CH₃ | —NH—C(C₂H₅)(cyclopentyl) | O | O | 233–234 |
| 53 | CH₃ | CH₃ | —NH—C(CN)(CH₃)—(4-chlorophenyl) | O | O | 220–221 |
| 54 | CH₃ | CH₃ | —NH—C(CN)(CH₃)—(4-fluorophenyl) | O | O | 208 (decomp.) |
| 55 | CH₃ | CH₃ | —NH—CH(CH₃)—CH=N—OCH₃ | O | O | 117–119 |
| 56 | CH₃ | CH₃ | —NH—C₂H₅ | O | S | 150–151 |
| 57 | CH₃ | CH₃ | —NH—(CH₂)₅—CH₂Cl | O | O | 106 |
| 58 | CH₃ | CH₃ | —NH—(2-chlorocyclohexyl) | O | O | 219–220 |
| 59 | CH₃ | CH₃ | —NH—CH(CH₃)—CH=CH—CHCl₂ | O | O | 174–176 |
| 60 | CH₃ | CH₃ | —NH—C(CH₃)₂—CH(CH₃)—CH=CCl₂ | O | O | 195–196 |
| 61 | CH₃ | CH₃ | —NH—C(CH₃)₂—CH=CCl₂ | O | O | 211–213 |
| 62 | CH₃ | CH₃ | —NH—CH(CH₂Cl)₂—NH—CH₂—CH(Cl)—CH₂Cl (60:40) | O | O | 162–163 |

TABLE 1-continued

| Example No | R¹ | R² | −N(R³)(R⁴) | X | Y | Melting point/°C |
|---|---|---|---|---|---|---|
| 63 | $CH_3$ | $CH_3$ | $-C(CH_3)(C_2H_5)CH_3$ | O | O | 221–222 |
| 64 | $CH_3$ | $CH_3$ | $-NH-(CH_2)_5-CH_3$ | O | O | 100–102 |
| 65 | $CH_3$ | $CH_3$ | $-NH-CH_2-CH(CH_3)_2$ | O | O | 155–157 |
| 66 | $CH_3$ | $CH_3$ | $-NH-CH_2-CH(C_2H_5)-(CH_2)_3-CH_3$ | O | O | 140–141 |
| 67 | $CH_3$ | $CH_3$ | $-NH-CH(CH_3)-(CH_2)_2-C_6H_5$ | O | O | 116–118 |
| 68 | $CH_3$ | $CH_3$ | $-NH-OCH_3$ | O | O | 167–170 |
| 69 | $CH_3$ | $CH_3$ | $-NH-CH_2-$ (2,2-dichlorocyclopropyl) | O | O | 182–183 |
| 70 | $CH_3$ | $CH_3$ | $-NH-CH(CH_3)-CH_2-CH(CH_3)_2$ | O | O | 170–173 |
| 71 | $CH_3$ | $CH_3$ | $-NH-CH_2-CH_2-CH(CH_3)_2$ | O | O | 116–120 |
| 72 | $CH_3$ | $CH_3$ | $-N(CH_3)(C_2H_5)$ | O | O | 109–111 |
| 73 | $CH_3$ | $CH_3$ | $-NH-$cycloheptyl | O | O | 203–206 |
| 74 | $CH_3$ | $CH_3$ | $-NH-$cyclobutyl | O | O | 173–176 |
| 75 | $CH_3$ | $CH_3$ | $-NH-CH_2-CH_2-C_6H_4-Cl$ (4-) | O | O | 173–175 |
| 76 | $CH_3$ | $CH_3$ | $-NH-CH_2-CH(CH_3)-C_2H_5$ | O | O | 156–158 |
| 77 | $CH_3$ | $CH_3$ | $-NH-$cyclopentyl | O | O | 187–189 |
| 78 | $CH_3$ | $CH_3$ | $-NH-CH_2-CH(CH_3)-C_6H_5$ | O | O | 63–65 |
| 79 | $CH_3$ | $CH_3$ | $-NH-(CH_2)_3-C_6H_5$ | O | O | 79–81 |

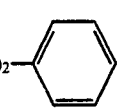

TABLE 1-continued

| Example No | $R^1$ | $R^2$ | $-N{-R^3 \atop R^4}$ | X | Y | Melting point/°C. |
|---|---|---|---|---|---|---|
| 80 | $CH_3$ | $CH_3$ | $-NH-(CH_2)_4-C_6H_5$ | O | O | 107–110 |
| 81 | $CH_3$ | $CH_3$ | $-NH-CH(CH_3)-(CH_2)_4-CH_3$ | O | O | 127–129 |
| 82 | $CH_3$ | $CH_3$ | $-NH-CH(CH_3)-(CH_2)_2-CH_3$ | O | O | 160–163 |
| 83 | $CH_3$ | $CH_3$ | $-NH-CH(CH_3)-CH(CH_3)_2$ | O | O | 222–223 |
| 84 | $CH_3$ | $CH_3$ | $-NH-CH(CH_3)-(CH_2)_3-CH(CH_3)_2$ | O | O | 159–161 |
| 85 | $CH_3$ | $CH_3$ | $-NH-CH(C_2H_5)-(CH_2)_3-CH_3$ | O | O | 150–151 |
| 86 | $CH_3$ | $CH_3$ | $-NH-CH(CH_3)-CH_2-OCH_3$ | O | O | 139–141 |
| 87 | $CH_3$ | $CH_3$ | $-NH-C(C_2H_5)(CH_3)(C_2H_5)$ | O | O | 226 |
| 88 | $CH_3$ | $CH_3$ | $-NH-C(C_2H_5)_3$ | O | O | 208–210 |
| 89 | $CH_3$ | $CH_3$ | $-NH-C(CH_3)_2-(CH_2)_3-CH_3$ | O | O | 136–187 |
| 90 | $CH_3$ | $CH_3$ | $-NH-C(CH_3)_2-CH_2-N(morpholino)$ | O | O | 159–161 |
| 91 | $CH_3$ | $CH_3$ | $-NH-CH(CN)-CH(CH_3)_2$ | O | O | 134–136 |
| 92 | $CH_3$ | $CH_3$ | $-NH-CH(CH_3)-CH(CH_3)-C_2H_5$ | O | O | 194–196 |
| 93 | $CH_3$ | $C_2H_5$ | $-NH-CH_3$ | O | O | 215–217 |
| 94 | $CH_3$ | $C_2H_5$ | $-NH-CH(CH_3)_2$ | O | O | 148–150 |
| 95 | $CH_3$ | $C_2H_5$ | $-NH-C(CH_3)_2-CH_2Cl$ | O | O | 176–178 |
| 96 | $CH_3$ | $C_2H_5$ | $-NH-C_6H_{11}$ | O | O | 185–187 |
| 97 | $CH_3$ | $C_2H_5$ | $-NH-CH(CH_3)-C_2H_5-$ | O | O | 143–145 |
| 98 | $CH_3$ | $(CH_3)_2CH-$ | $-NH-CH_3$ | O | O | 184–187 |

TABLE 1-continued

| Example No | R¹ | R² | —N—R³ \| R⁴ | X | Y | Melting point/°C. |
|---|---|---|---|---|---|---|
| 99 | CH₃ | (CH₃)₂CH— | —NH—CH(CH₃)₂ | O | O | 184–185 |
| 100 | CH₃ | (CH₃)₂CH— | —NH—CH—C₂H₅ \| CH₃ | O | O | 189–191 |

PREPARATION OF THE STARTING MATERIALS

Example II-1

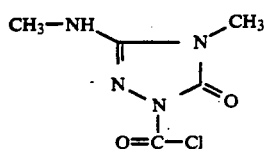

12.8 g (0.1 mol) of 3-methylamino-4-methyl-(1H)-1,2, 4-triazolin-5-one are added to a saturated solution of about 150 g of phosgene in 150 ml of dry chlorobenzene, and the stirred mixture is heated to reflux temperature while more phosgene is passed in. After 30 minutes, excess phosgene is expelled from the solution with the aid of a dry stream of nitrogen, and the cold precipitated product is filtered off with suction under cold conditions and recrystallized from ethyl acetate.

This gives 17.5 g (92% of theory) of 1-chlorocarbonyl-3-methylamino-4-methyl-1,2, 4-triazolin-5-one of melting point 185° C.

Example IV-1

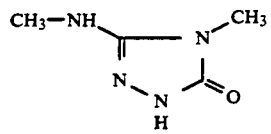

87 g (0.6 mol) of 3-methylthio-4-methyl-(1H)-1,2, 4-triazolin-5-one (cf., for example, U.S. Pat. No. 4,098,896 or U.S. Pat. No. 4,110,332) and 300 g (9.67 mol) of methylamine in 1,000 ml of ethanol are heated in a 3,000 ml autoclave with stirring for 3 hours at 230° C., during which process a pressure of 75 bar is established. When cold, the reaction mixture is evaporated, and the residue is recrystallized from acetonitrile.

This gives 58 g (76% of theory) of 3-methylamino-4-methyl-(1H)-1,2, 4-triazolin-5-one of melting point 202°–204° C.

Example IV-2

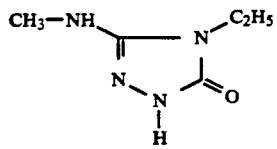

45.75 g (0.3 mol) of 1-amino-2,2, 3-trimethylguanidinium hydrochloride (cf., for example, European Patent 283,876) and 21.3 g (0.3 mol) of ethyl isocyanate are stirred for 2 hours at reflux temperature in 300 ml of acetonitrile, the mixture is subsequently cooled to 40° C., 50.4 g (0.6 mol) of sodium hydrogen carbonate are added, and the mixture is stirred for 8 more hours at reflux temperature. For working up, the hot mixture is filtered, and the filtrate is cooled. The reaction product which has precipitated is filtered off with suction, washed and dried.

This gives 25 g (59% of theory) of 3-methylamino-4-ethyl-(1H)-1,2, 4-triazolin-5-one of melting point 208°–210° C.

Example IV-3

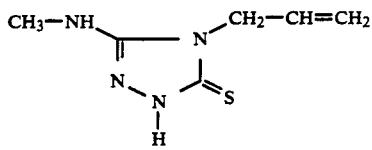

91.5 g (0.6 mol) of 1-amino-2,2, 3-trimethylguanidinium hydrochloride and 59.4 g (0.6 mol) of allyl isothiocyanate are stirred for 2 hours at reflux temperature in 800 ml of acetonitrile; 60.6 g (0.6 mol) of triethylamine are subsequently added, the mixture is stirred for one more hour at reflux temperature, cooled and filtered, the filtrate is concentrated, and the oily residue is distributed between dichloromethane and water. The combined organic phases are dried over sodium sulphate and evaporated.

This gives 68 g (67% of theory) of 3-methylamino-4-allyl-(1H)-1,2, 4-triazolin-5-thione of melting point 129°–131° C.

Example VIIb-1

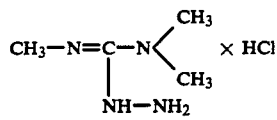

A solution of 78.5 g (0.5 mol) of chlorotrimethylformamidinium hydrochloride in 250 ml of isopropanol is added dropwise with stirring at 20° C. to 25° C. in the course of 30 minutes to 50 g (1 mol) of hydrazine hydrate in 300 ml of isopropanol; when the addition is complete, the mixture is stirred for a further 30 minutes at room temperature, hydrazine hydrochloride which has precipitated is filtered off with suction and rinsed with 150 ml of isopropanol, and the isopropanol filtrate is evaporated in vacuo.

This gives 70.7 g (93% of theory) of 1-amino-2,2,3-trimethylguanidinium hydrochloride, which is reacted further without purification.

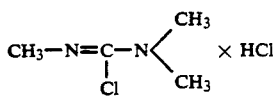

545 g (5.5 mol) of phosgene are passed at 80° C. in the course of 2.5 hours into a stirred mixture of 510 g (5 mol) of N,N,N'-trimethylurea and 3 liters of chlorobenzene; when all the phosgene has been passed in, stirring is continued for 45 minutes at 80° C. until the evolution of carbon dioxide has ceased. The reaction mixture is cooled to 10° C., and the product, which is sensitive to water, is filtered off with suction under nitrogen, washed with 1 liter of chlorobenzene and twice with 500 ml portions of petroleum ether and dried in vacuo.

This gives 635.3 g (81% of theory) of chlorotrimethylformamidinium hydrochloride of melting point 76° C. to 78° C.

USE EXAMPLES

In the use example which follows, the compound listed below was employed as comparison substance:

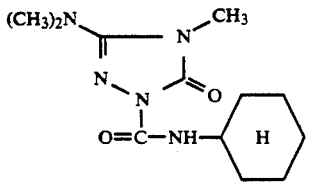

1-Cyclohexylaminocarbonyl-3-dimethylamino-4-methyl-1,2,4-triazolin-5-one (known from European Patent 283,876).

EXAMPLE A

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control.

The figures denote:
0% = no action (like untreated control)
100% = total destruction In this test, the compounds of Preparation Examples 7, 12, 29, 48 and 69 show a clearly superior herbicidal activity compared with compound (A) which is known from the prior art, while having a comparably good selectivity towards crop plants.

It is understood that the specification and examples are illustrative but not limitative of the present invention and that other embodiments within the spirit and scope of the invention will suggest themselves to those skilled in the art.

We claim:
1. A substituted triazolone of the formula

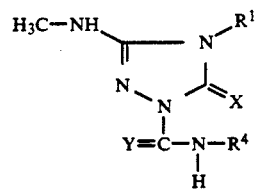

in which
R$^1$ represents hydrogen, or represents in each case straight-chain or branched alkyl having 1 to 8 carbon atoms, alkenyl having 2 to 8 carbon atoms, alkynyl having 2 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, halogenoalkynyl having 2 to 8 carbon atoms and 1 to 13 identical or different halogen atoms, alkoxyalkyl or alkoxy each of which has 1 to 6 carbon atoms in the individual alkyl moieties, or represents cycloalkylalkyl or cycloalkyl each of which has 3 to 7 carbon atoms in the cycloalkyl moiety and, if appropriate, 1 to 6 carbon atoms in the straight-chain or branched alkyl moiety, or represents aralkyl or aryl each of which has 6 to 10 carbon atoms in the aryl moiety and, if appropriate, 1 to 6 carbon atoms in the straight-chain or branched alkyl moiety and each of which is optionally monosubstituted or polysubstituted on the aryl by identical or different substituents selected from the group consisting of halogen, cyano, nitro, straight-chain or branched alkyl, alkoxy, alkylthio, halogenoalkyl, halogenoalkoxy and halogenoalkylthio each of which has 1 to 4 carbon atoms and, if appropriate, 1 to 9 identical or different halogen atoms, and R$^4$ represents alkyl having 1 to 18 carbon atoms, alkenyl having 2 to 8 carbon atoms, alkynyl having 2 to 8 carbon atoms, halogenaoalkyl having 1 to 8 carbon atoms and 1 to 17 identical or different halogen atoms, halogenoalkenyl or halogenoalkynyl each of which has 2 to 8 carbon atoms and 1 to 15 identical or different halogen atoms, alkoximinoalkyl each of which has 1 to 8 carbon atoms in the individual alkyl moieties, or represent cycloalkyl or cycloalkylalkyl, each of which has 3 to 8 carbon atoms in the cycloalkyl moiety and 1 to 6 carbon atoms in the alkyl moiety and each of which is optionally monosubstituted or polysubstituted by halogen.

2. A substituted triazolone according to claim 1, in which

R$^1$ represents hydrogen, methyl, ethyl, n- or i-propyl, n-, i-, s- or t-butyl, n- or i-pentyl or n- or i-hexyl, or represents allyl, propargyl, methoxy, ethoxy or methoxymethyl, or represents straight-chain or branched halogenoalkyl having 1 to 4 carbon atoms and 1 to 9 identical or different halogen atoms, or represents cyclopentyl, cyclohexyl, cyclopropyl, cyclopropylmethyl, cyclohexylmethyl or cyclohexylethyl, or represents benzyl or phenyl, each of which is optionally monosubstituted to trisubstituted by identical or different substituents selected from the group consisting of fluorine, chlorine, bromine, cyano, nitro, methyl, ethyl, n- or i-propyl, n-, i-, s- or t-butyl, methoxy, ethoxy, methylthio, trifluoromethyl, trifluoromethoxy and trifluoromethylthio, and R⁴ represents hydrogen, methyl, ethyl, n- or i-propyl, n-, i-, s- or t-butyl, n- or i-pentyl, n- or i-hexyl, n- or i-heptyl, n- or i-octyl, n- or i-nonyl, n- or i-decyl, n- or i-dodecyl, or represents allyl, n- or i-butenyl, n- or i-pentenyl, n- or i-hexynyl, propargyl, n- or i-butynyl, n- or i-pentynyl, n- o. i-hexynyl, or represents straight-chain or branched halogenoalkyl having 1 to 6 carbon atoms and 1 to 9 identical or different halogen atoms, or represents in each case straight-chain or branched halogenoalkenyl or halogenoalkynyl, each of which has 3 to 8 carbon atoms and 1 to 3 halogen atoms, or represent in each case optionally straight-chain or branched methoximinoalkyl or ethoximinoalkyl, each of which has 1 to 5 carbon atoms in the alkyl moiety, or represent cyclopropyl, cyclopropylmethyl, cyclopropylethyl, cyclopentyl, cyclohexyl, cycloheptyl, cyclooctyl, cyclohexylmethyl or cyclohexylethyl, each of which is optionally mono-substituted to trisubstituted by identical or different substituents selected from the group consisting of fluorine, chlorine and bromine.

3. A herbicidal composition comprising a herbicidally effective amount of a compound according to claim 1, and an inert diluent.

4. A method of combating unwanted vegetation which comprises applying to such vegetation or to a locus from which it is desired to exclude such vegetation a herbicidally effective amount of a compound according to claim 1.

5. A substituted triazolone of the formula

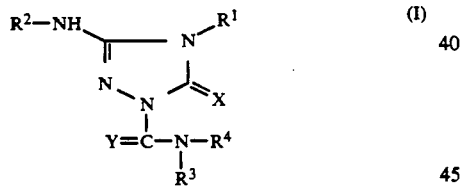

(I)

in which
R¹ represents hydrogen, or represents in each case straight-chain or branched alkyl having 1 to 8 carbon atoms, alkenyl having 2 to 8 carbon atoms, alkynyl having 2 to 8 carbon atoms, halogenoalkyl having 1 to 8 carbon atoms and 1 to 17 identical or different halogen atoms, halogenoalkenyl having 2 to 8 carbon atoms and 1 to 15 identical or different halogen atoms, halogenoalkynyl having 2 to 8 carbon atoms and 1 to 13 identical or different halogen atoms, alkoxyalkyl or alkoxy each of which has 1 to 6 carbon atoms in the individual alkyl moieties, or represents cycloalkylalkyl or cycloalkyl each of which has 3 to 7 carbon atoms in the cycloalkyl moiety and, if appropriate, 1 to 6 carbon atoms in the straight-chain or branched alkyl moiety, or represents aralkyl or aryl each of which has 6 to 10 carbon atoms in the aryl moiety and, if appropriate, 1 to 6 carbon atoms in the straight-chain or branched alkyl moiety and each of which is optionally monosubstituted or polysubstituted on the aryl by identical or different substituents selected from the group consisting of halogen, cyano, nitro, straight-chain or branched alkyl, alkoxy, alkylthio, halogenoalkyl, halogenoalkoxy and halogenoalkylthio each of which has 1 to 4 carbon atoms and, if appropriate, 1 to 9 identical or different halogen atoms, R² represents in each case straight-chain or branched alkyl having 2 to 8 carbon atoms, alkenyl having 2 to 8 carbon atoms, alkynyl having 2 to 8 carbon atoms, halogenoalkyl having 1 to 8 carbon atoms and 1 to 17 identical or different halogen atoms, halogenoalkenyl or halogenoalkynyl each of which has 2 to 8 carbon atoms and 1 to 15 identical or different halogen atoms, alkoxyalkyl or alkoxy, each of which has 1 to 6 carbon atoms in the individual alkyl moieties, or represents cycloalkyl having 3 to 7 carbon atoms, or represents cycloalkylalkyl having 3 to 7 carbon atoms in the cycloalkyl moiety and 1 to 6 carbon atoms in the alkyl moiety, or represents aralkyl which has 6 to 10 carbon atoms in the aryl moiety and 1 to 6 carbon atoms in the alkyl moiety and which is optionally monosubstituted or polysubstituted by identical or different substituents, in the aryl moiety aryl which has 6 to 10 carbon atoms and which is optionally monosubstituted or polysubstituted by identical or different substituents, the substituents in the aryl moiety being selected from the group consisting of halogen, cyano, nitro, straight-chain or branched alkyl, alkoxy, alkylthio, halogenoalkyl, halogenoalkoxy and halogenoalkylthio, each of which has 1 to 4 carbon atoms and if appropriate 1 to 9 identical or different halogen atoms, R³ and R⁴ independently of one another each represents hydrogen, or represent in each case straight-chain or branched alkyl having 1 to 18 carbon atoms, alkenyl having 2 to 8 carbon atoms, alkynyl having 2 to 8 carbon atoms, halogenoalkyl having 1 to 8 carbon atoms and 1 to 17 identical or different halogen atoms, halogenoalkenyl or halogenoalkynyl each of which has 2 to 8 carbon atoms and 1 to 15 identical or different halogen atoms, cyanoalkyl having 1 to 8 carbon atoms, hydroxyalkyl having 1 to 8 carbon atoms and 1 to 6 hydroxyl groups, alkoxyalkyl, alkoxycarbonylalkyl or alkoxycarbonylalkenyl each of which has up to 6 carbon atoms in the individual alkyl or alkenyl moieties, or represent alkylaminoalkyl, dialkylaminoalkyl or alkoximinoalkyl each of which has 1 to 8 carbon atoms in the individual alkyl moieties, or represent cycloalkyl, cycloalkylalkyl, cycloalkenyl or cycloalkenylalkyl each of which has 3 to 8 carbon atoms in the cycloalkyl or cycloalkenyl moiety and if appropriate 1 to 6 carbon atoms in the alkyl moiety and each of which is optionally monosubstituted or polysubstituted by identical or different substituents selected from the group consisting of halogen, cyano, straight-chain or branched alkyl or halogenoalkyl each of which has 1 to 4 carbon atoms and if appropriate 1 to 9 identical or different halogen atoms or in each case double-linked alkanediyl or alkenediyl each of which has up to 4 carbon atoms;

R³ and R⁴ furthermore independently of one another represent in each case straight-chain or branched alkoxy having 1 to 8 carbon atoms, alkenyloxy having 2 to 8 carbon atoms or alkynyloxy having 2 to 8 carbon atoms, and finally represent aralkyl, aralkyloxy, aryloxy, aroyl or aryl, each of which has 6 to 10 carbon atoms in the aryl moiety and if appropriate 1 to 6 carbon atoms in the alkyl moiety and each of which is optionally monosubstituted or polysubstituted on the aryl by identical or different substituents selected from the group consisting of halogen, cyano, nitro, hydroxyl, straight-chain or branched alkyl, alkoxy, alkylthio, halogenoalkyl, halogenoalkoxy, halogenoalkylthio, alkylsulphinyl, alkylsulphonyl, halogenoalkylsulphinyl, halogenoalkylsulphonyl, alkanoyl or alkoxycarbonyl each of which has 1 to 6 carbon atoms and if appropriate 1 to 9 identical or different halogen atoms, cycloalkyl having 3 to 6 carbon atoms and phenoxy, the alkyl moieties optionally being substituted by halogen or cyano, X represents oxygen or sulphur and Y represents oxygen or sulphur.

6. A substituted triazolone according to claim 5, in which $R^1$ represents hydrogen, methyl, ethyl, n- or i-propyl, n-, i-, s- or t-butyl, n- or i-pentyl or n- or i-hexyl, or represents allyl, propargyl, methoxy, ethoxy or methoxymethyl, or represents straight-chain or branched halogenoalkyl having 1 to 4 carbon atoms and 1 to 9 identical or different halogen atoms, or represents cyclopentyl, cyclohexyl, cyclopropyl, cyclopropylmethyl, cyclohexylmethyl or cyclohexylethyl, or represents benzyl or phenyl, each of which is optionally monosubstituted to trisubstituted by identical or different substituents selected from the group consisting of fluorine, chlorine, bromine, cyano, nitro, methyl, ethyl, n- or i-propyl, n-, i-, s- or t-butyl, methoxy, ethoxy, methylthio, trifluoromethyl, trifluoromethoxy and trifluoromethylthio, $R^2$ represents ethyl, n- or i-propyl, n-, i-, s- or t-butyl, n- or i-pentyl, allyl or propargyl, or represents in each case straight-chain or branched halogenoalkyl having 1 to 4 carbon atoms, halogenoalkenyl having 3 to 6 carbon atoms or halogenoalkynyl having 3 to 6 carbon atoms and in each case 1 to 9 identical or different halogen atoms, or represents methoxymethyl, methoxyethyl, methoxy or ethoxy, or represents cyclopropyl, cyclopropylmethyl, cyclopentyl, cyclohexyl, cyclohexylmethyl, cyclohexylethyl or cyclopentylmethyl, or represents benzyl, phenylethyl or phenyl, each of which is optionally monosubstituted to trisubstituted by identical or different substituents selected from the group consisting of fluorine, chlorine, bromine, cyano, nitro, methyl, ethyl, n- or i-propyl, n-, i-, s- or t-butyl, methoxy, ethoxy, methylthio, trifluoromethyl, trifluoromethoxy and trifluoromethylthio, $R^3$ and $R^4$ independently of one another each represents hydrogen, methyl, ethyl, n- or i-propyl, n-, i-, s- or t-butyl, n- or i-pentyl, n- or i-hexyl, n- or i-heptyl, n- or i-octyl, n- or i-nonyl, n- or i-decyl, n- or i-dodecyl, or represents allyl, n- or i-butenyl, n- or i-pentenyl, n- or i-hexenyl, propargyl, n- or i-butynyl, n- or i-pentynyl, n- or i-hexynyl, or represent straight-chain or branched halogenoalkyl having 1 to 6 carbon atoms and 1 to 9 identical or different halogen atoms, or represent in each case straight-chain or branched halogenoalkenyl or halogenoalkynyl, each of which has 3 to 8 carbon atoms and 1 to 3 halogen atoms, or represent in each case straight-chain or branched cyanoalkyl having 1 to 6 carbon atoms in the alkyl moiety, hydroxyalkyl having 1 to 6 carbon atoms and 1 to 3 hydroxyl groups, alkoxyalkyl, alkoxycarbonylalkyl or alkoxycarbonylalkenyl, alkylaminoalkyl or dialkylaminoalkyl, each of which has up to 4 carbon atoms i the individual alkyl or alkenyl moieties, or represent in each case optionally straight-chain or branched methoximinoalkyl or ethoximinoalkyl, each of which has 1 to 5 carbon atoms in the alkyl moiety, or represent cyclopropyl, cyclopropylmethyl, cyclopropylethyl, cyclopentyl, cyclohexyl, cycloheptyl, cyclooctyl, cyclohexylmethyl, .cyclohexylethyl, cyclohexenyl or cyclohexenylmethyl, each of which is optionally monosubstituted to trisubstituted by identical or different substituents selected from the group consisting of fluorine, chlorine and bromine, methyl, ethyl, n- or i-propyl, n-, i-, s- or t-butyl, cyano, methanediyl, ethanediyl, butanediyl and butadienediyl, X represents oxygen or sulphur and Y represents oxygen or sulphur.

7. A compound according to claim 1, wherein such compound is 1-cyclohexylaminocarbonyl-3-methylamino-4-methyl-1,2, 4-triazolin-5-one of the formula

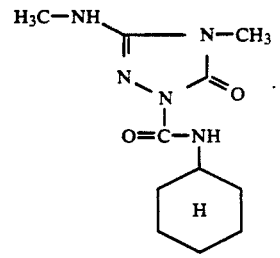

8. A compound according to claim 1, wherein such compound is 1-monochloro-t-butyl-aminocarbonyl-3-methylamino-4-methyl-1,2,4-triazolin-5-one of the formula

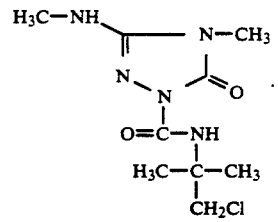

9. A compound according to claim 1, wherein such compound is 1-(sec-butylaminocarbonyl)-3-methylamino-4-methyl-1,2,4-triazolin-5-one of the formula

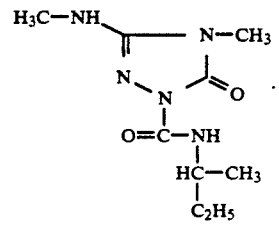

10. A compound according to claim 1, wherein such compound is 1-(2-ethynyl-prop-2-ylaminocarbonyl)-3methylamino-4-methyl-1,2,4-triazolin-5-one of the formula

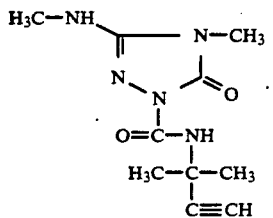

11. A compound according to claim 1, wherein such compound is 1-(2,2-dichlorocyclopropyl-methylaminocarbonyl) -3-methylamino-4-methyl-1,2,4-triazolin-5-one the formula

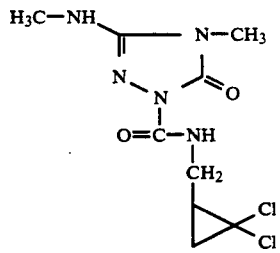

12. A herbicidal composition comprising a herbicidally effective amount of a compound according to claim 5, and an inert diluent.

13. A method of combating unwanted vegetation which comprises applying to such vegetation or to a locus from which it is desired to exclude such vegetation a herbicidally effective amount of a compound according to claim 5.

14. The method according to claim 4, wherein such compound is
1-cyclohexylaminocarbonyl-3-methylamino-4-methyl -1,2,4-triazolin-5-one,
1-monochloro-t-butyl-aminocarbonyl-3-methylamino-4-methyl-1,2,4-triazolin-5-one,
1-(sec-butylaminocarbonyl)-3-methylamino-4-methyl-1,2,4-triazolin-5-one,
1-(2-ethynyl-prop-2-ylaminocarbonyl)-3-methylamino-4-methyl-1,2,4-triazolin-5-one or
1-(2,2-dichlorocyclopropyl-methylaminocarbonyl) -3-methylamino-4-methyl-1,2,4-triazolin-5-one.

* * * * *